United States Patent [19]

Jourdan

[11] 4,088,458
[45] May 9, 1978

[54] HEATER BLOCK FOR LOW COST GAS CHROMATOGRAPH

[75] Inventor: Paul I. Jourdan, Houston, Tex.

[73] Assignee: Honeywell Inc., Minneapolis, Minn.

[21] Appl. No.: 764,769

[22] Filed: Feb. 2, 1977

[51] Int. Cl.² ............................................. B01D 15/08
[52] U.S. Cl. ........................................ 55/197; 53/269; 53/386
[58] Field of Search ............... 55/197, 386, 208, 267, 55/269

[56] References Cited

U.S. PATENT DOCUMENTS

| | | | |
|---|---|---|---|
| 3,309,504 | 3/1967 | Rosso et al. | 55/386 X |
| 3,364,659 | 1/1968 | Pierrard et al. | 55/197 |

*Primary Examiner*—John Adee
*Attorney, Agent, or Firm*—Laurence J. Marhoefer; Lockwood D. Burton

[57] ABSTRACT

In a gas chromatograph assembly, a heat conducting block of relatively large mass has a plurality of cavities formed therein. One cavity houses the chromatographic column; another cavity, extending into close proximity to the first, houses a temperature sensing element; and a third cavity houses a heater. This assembly is secured to a heat transmitting base to which is also secured an explosion-proof housing which houses a detector block. The entire assembly is covered with insulation and the heater block maintains the chromatographic column and the detector block at substantially the same temperature.

4 Claims, 3 Drawing Figures

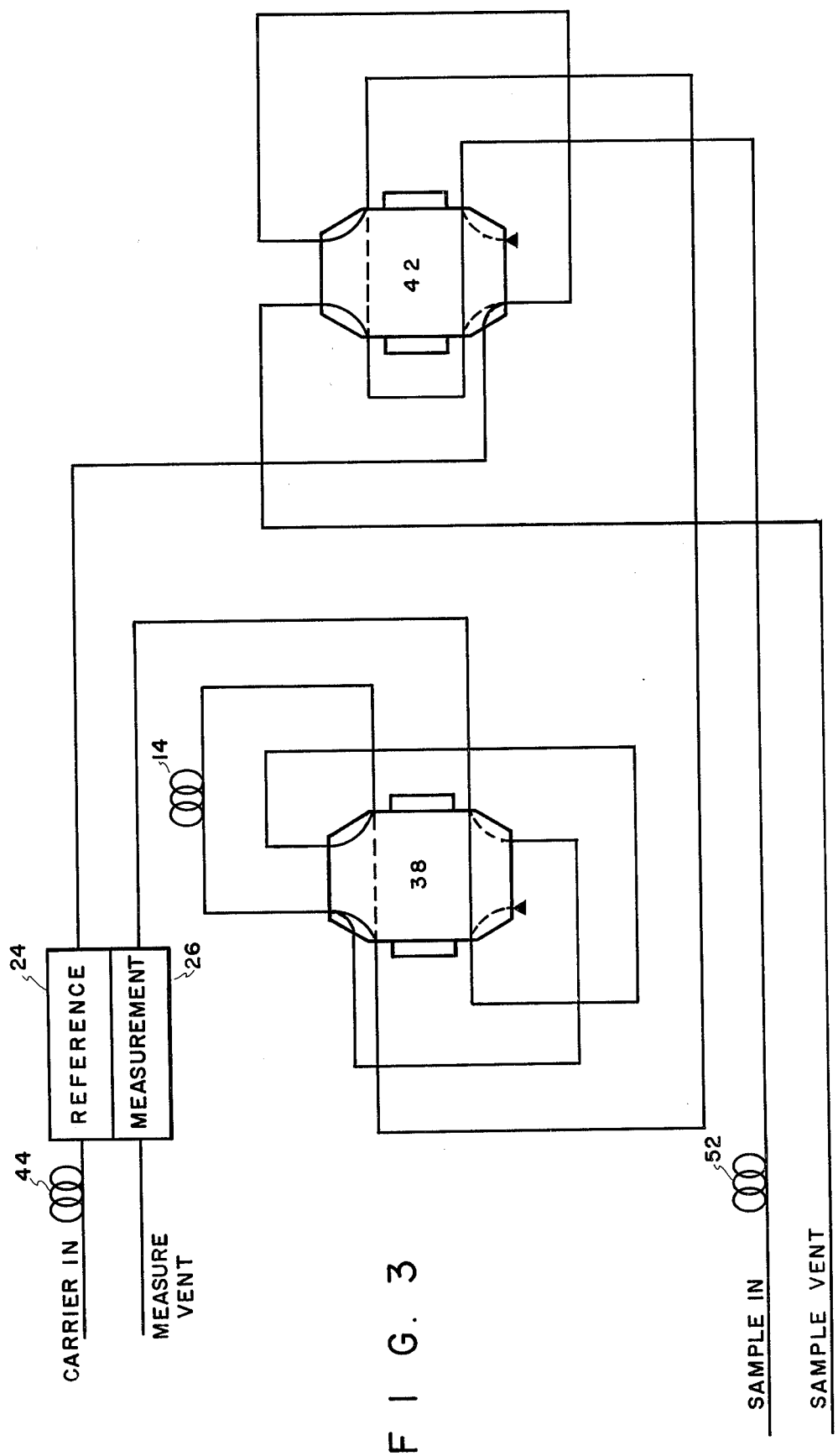

HEATER BLOCK FOR LOW COST GAS CHROMATOGRAPH

BACKGROUND OF THE INVENTION

This invention relates to a heater block chromatographic assembly for instrumentation and, more particularly, to a novel and improved assembly of relatively low cost as compared to prior art assemblies of equivalent performance.

DESCRIPTION OF THE PRIOR ART

In a gas chromatograph of the type to which the present invention relates, chromatographic separation of components is accomplished by injecting a precise amount of vapor sample onto an analytical column. A carrier gas (mobile phase) transports the sample through the column which contains a suitable packing (stationary phase) consisting of either an active solid (absorption partitioning) or a liquid phase coating on an inert solid support (adsorption partitioning). In either case, selective retardation of the sample component gases takes place within the column so that the components move through the column at different rates thus producing the desired separation. A thermal conductivity detector senses the elute of components from the column and produces electrical outputs proportional to the component concentration. This electrical output signal is preamplified and then routed to a data control electronics for further processing and display.

The thermal conductivity detector consists of a balanced bridge network, for example, with heat sensitive thermistors in each leg of the bridge. The two thermistors, one designated the "reference element" and the other as the "measurement element" are each enclosed in separate chambers of a detector block. In a quiescent condition (i.e., prior to injecting a sample), both legs of the bridge are exposed to the pure carrier gas. In this condition, the bridge is balanced and the bridge output it electrically nulled. Analysis begins when a fixed volume of sample is injected onto the column by means of a sample valve. The sample is transported through the column by the continuous flow of carrier gas. As successive components elute from the column, the temperature of the measurement gas changes, thus unbalancing the bridge and producing an electrical output proportional to the component concentration. It is this electrical output which is preamplified and routed to the data control electronics for recording on a strip chart recorder, for example.

As those skilled in the art will readily appreciate, it is necessary for a proper operation of the chromatograph that the temperature of the gas throughout the column be constant and, in addition, that the column temperature be approximately the same temperature as the chambers of the detector block which house the reference element and the measurement element. In prior art chromatographs, this has been accomplished by controlling the temperature in the detector block and controlling the temperature of the separation column. While this prior art approach has proved generally satisfactory, it is costly to implement in that it requires a number of heating elements, a number of sensing elements, and associated control electronics for each.

SUMMARY OF THE INVENTION

The object of this invention is to provide a heater block assembly in which a single heater and controller maintain a uniform temperature in the column. In addition, this same heater block assembly maintains the same temperature of the detector block and sample loop at column temperature.

Briefly this invention contemplates the provision of a heater block assembly comprising a block of heat conducting material in which a plurality of cavities are formed. The separation column is disposed in one cavity; preheat coils are located in respective other cavities; and an electrical resistance heater and a temperature sensor are located in two other cavities closely adjacent the separation column. As an adjunct of this invention, the block is of sufficient thermal mass that it maintains constant the temperature of a detector block located in an explosion-proof housing adjacent the heater block and a sample loop located near the heater block.

BRIEF DESCRIPTION OF THE DRAWINGS

A better understanding of the present invention may be had from the following detailed description when read in connection with the accompanying drawings in which:

FIG. 3 is a schematic diagram of a gas chromatograph which may employ a heater block constructed in accordance with the teachings of this invention.

DETAILED DESCRIPTION

Figure 1:
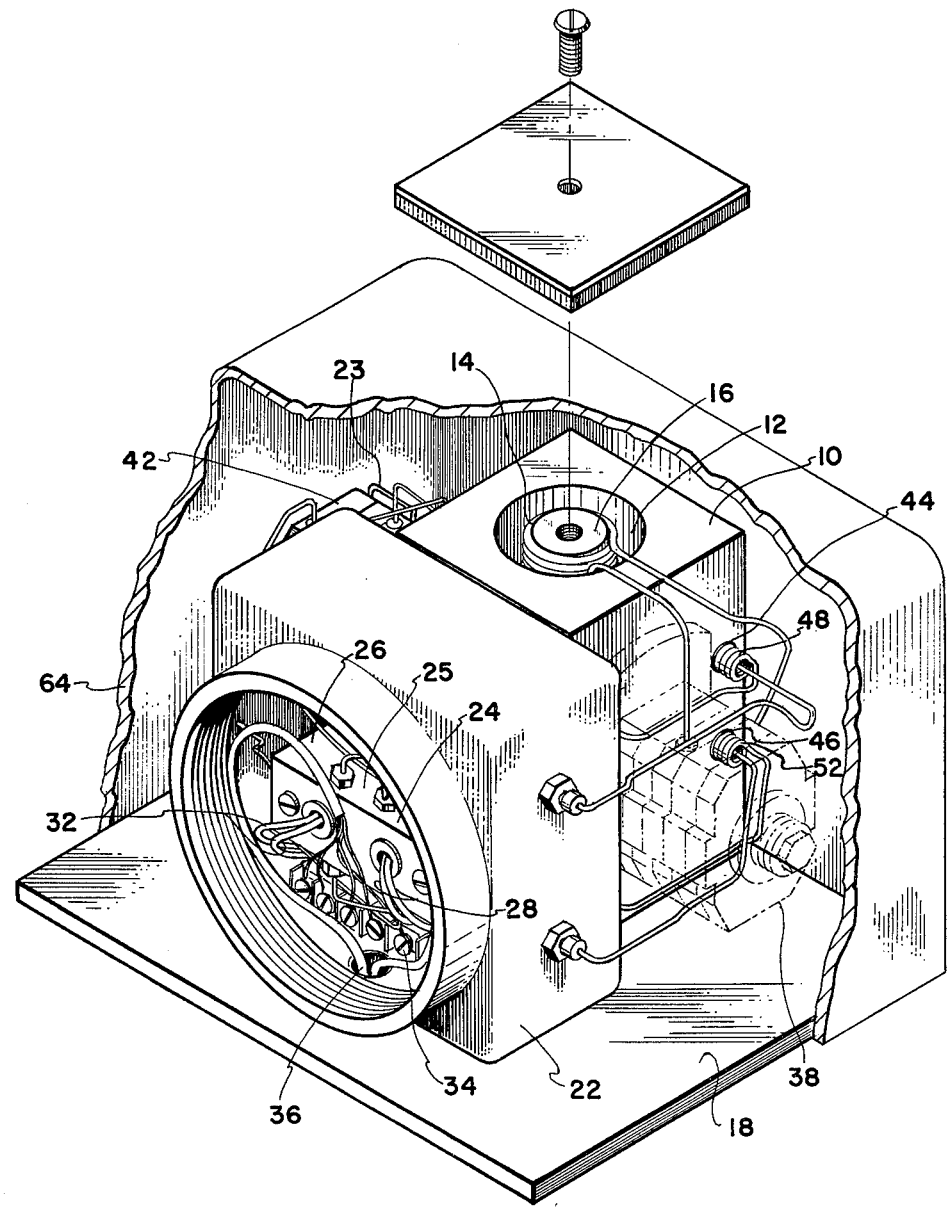
FIG. 1 is an isometric view of a heater block assembly and detector block located adjacent thereto in an explosion-proof housing.

Referring now to FIG. 1 of the drawings, a heater block 10, preferably of cast aluminum, has a centrally disposed cavity 12 for housing a chromatograph column 14. The column 14 wraps around an aluminum plug 16 which conveniently is formed integrally with the block 10.

The heater block 10 rests upon and is suitably secured to an aluminum heat transfer plate 18 upon which also rests an explosion-proof housing 22 of suitable ferrous material. The housing 22 contains dual cavity detector block 25 in which is disposed a reference thermistor 24 (not shown) and a measurement thermistor 26 (not shown).

As will be appreciated by those skilled in the art, tubes conduct a carrier gas across the reference thermistor 24 within the block 25 and tubes conduct a sample gas across the measurement thermistor 26 in the block 25. The electrical output signals of these thermistors are connected by wires 28 and 32 to a terminal block 34 and this terminal block in turn is coupled by leads 36 to the external electronic detection package (not shown) which conveniently may be located directly below the explosion-proof housing.

Attached on one side of the heater block 10 is a sample valve 42 and on the other side a back flush valve 38. As will be appreciated by those skilled in the art, the sample valve 42 and back flush valve 38 control the flow of the sample gas and carrier gas through the chromatographic column 14. The external connections to these valves for the sample gas and the carrier gas are not shown in FIG. 1 but are representative schematically in FIG. 3.

A pair of cavities 44 and 46 in the heater block 10 house, respectively, a pair of preheater coils 48 and 52. This arrangement allows the carrier gas and the sample gas flows to be heated up to the operating temperature of the column prior to entering the column and thus insures that the gas is at a relatively constant temperature as it passes through the column and also as it passes through the sample loop 23.

Figure 2:
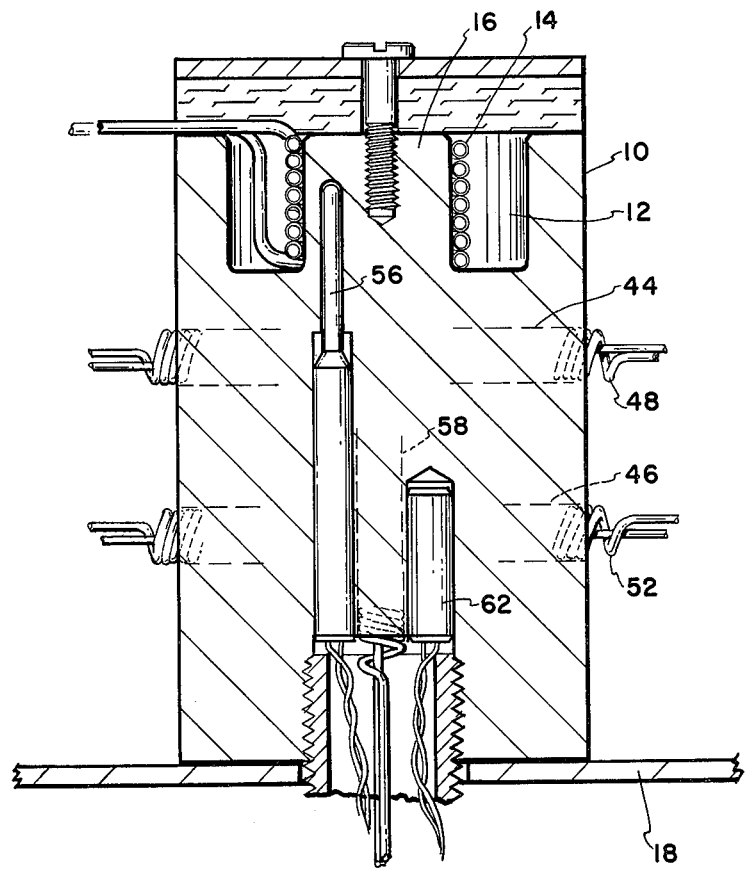
FIG. 2 is a detailed view with parts in section of a heater block in accordance with the teachings of this invention.

Referring now to FIG. 2, a temperature sensing thermistor 56 is disposed in another cavity in block 10 with its tip extending into the plug 16 so that it is in close proximity to the separation column 14. A pair of adjacent heating elements 58 (only one of which appears in the drawing) are centrally disposed in yet another cavity in the heater block 10. Each of these heating elements 58 conveniently may comprise a coil of high resistance wire, such as that in a cartridge heater. Disposed in the block 10 adjacent the heaters 58 is an over-temperature switch 62 which provides protection from overheating. The over-temperature switch 62 de-energizes the heaters 52 in the event the temperature of the block exceeds a predetermined temperature.

Electrical leads couple the temperature sensitive thermistor, the heater elements 58 and the over-temperature switch 62 to suitable electronic circuits located remotely from the block 10. These circuits, which are well known to those skilled in the art, control the amount of current flowing in the heater elements 58 in accordance with the temperature indicated by the thermistor 56. In the event of a malfunction which causes the temperature to exceed a predetermined amount, the over-temperature switch provides a signal which causes a de-energization of the heater coils 58.

Referring back to FIG. 1, the entire assembly of valves, coil, heating block and explosion-proof detector housing, is surrounded by a layer of thermal insulation 64. Conveniently, this thermal insulating cover 64 can be made in several panels in order to facilitate assembly and/or removal from the system. With this insulation, the heater block 10 can maintain constant the temperature of the detector blocks at approximately the temperature of the separation column. In a typical application, the block 10 may be about four inches long and two and three- quarter inches wide with a weight of about 2.5 pounds.

FIG. 3 is a schematic diagram of one mode in which the chromatograph of this invention can be operated — the mode shown in a back flush to measure mode. It will be appreciated that the apparatus of the invention can be operated in any of the flow configurations known in the art.

In the back flush to measure configuration shown in FIG. 3, the sample valve injects a sample into the column at the beginning of analysis and the back flush valve reverses the flow of the carrier gas through the column after the first component of interest has eluted. Back flushing the column allows slow eluting sample components to be routed through the detector for display as a single, combined peak, thus reducing the overall analysis time.

In the back flush to vent configuration, two components of interest elute from the column while the heavier components are back flushed to vent before reaching the final column. As the basic chromatographic scheme employed with the apparatus of this invention is well known in the art as is the operation of the sample and back flush valves, no detailed description of this operation will be given here.

As can be seen from an inspection of FIG. 3, the carrier gas input passes first through the preheater coil 44 and then the reference thermistor 24. Similarly, the sample gas input passes first through the preheater 52 and then is combined with the carrier gas via valve 42 and this combined flow eventually passes through the column 14. The output of the column 14 then passes over the measurement thermistor 26 and thereafter is vented to the atmosphere. It will be appreciated that as the measurement is basically a temperature measurement it is important to the operation that all components be at the same temperature and be maintained at a constant temperature. This is accomplished with the novel apparatus of this invention.

The embodiments of the invention in which an exclusive property or privilege is claimed are defined as follows:

1. In a gas chromatograph, an assembly comprising:
   (a) a solid heat conducting block;
   (b) a first cavity in said block housing a chromatographic column;
   (c) a second cavity in said block extending into close proximity to said first cavity and housing a temperature sensing element which can transmit an electrical signal whose magnitude is a function of the sensed temperature; and
   (d) a third cavity extending into close proximity of said second cavity and housing an electrically controllable heating element.

2. A gas chromatograph assembly as set forth in claim 1 including a fourth cavity in said block receiving a preheating coil for heating a gas to approximately the temperature of said chromatographic column prior to the entry of said gas into said column.

3. In a gas chromatograph, an assembly comprising:
   (a) a solid heat conducting block;
   (b) a first cavity in said block housing a chromatographic column;
   (c) a second cavity in said block extending into close proximity to said first cavity and housing a temperature sensing element which can transmit an electrical signal whose magnitude is a function of the sensed temperature;
   (d) a third cavity extending into close proximity of said second cavity and housing an electrically controllable heating element;
   (e) a heat conducting base;
   (f) a detector block;
   (g) an explosion-proof casing surrounding said detector block; and
   (h) said heat conducting block and said explosion-proof casing mounted on said heat conducting plate in close proximity to one another, whereby said chromatographic column and said detector block are maintained at approximately the same temperature by said heater.

4. A gas chromatograph assembly as set forth in claim 3 including a fourth cavity in said block receiving a preheating coil for heating a gas to approximately the temperature of said chromatographic column prior to the entry of said gas into said column.

* * * * *